United States Patent
Lange

(10) Patent No.: US 9,612,209 B2
(45) Date of Patent: *Apr. 4, 2017

(54) APPARATUS AND METHODS FOR DETECTING DEFECTS IN VERTICAL MEMORY

(71) Applicant: KLA-Tencor Corporation, Milpitas, CA (US)

(72) Inventor: Steven R. Lange, Alamo, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 9 days.

This patent is subject to a terminal disclaimer.

(21) Appl. No.: 14/728,938

(22) Filed: Jun. 2, 2015

(65) Prior Publication Data

US 2015/0260660 A1 Sep. 17, 2015

Related U.S. Application Data

(63) Continuation of application No. 14/078,271, filed on Nov. 12, 2013, now Pat. No. 9,075,027.

(Continued)

(51) Int. Cl.
*G01N 21/00* (2006.01)
*G01N 21/95* (2006.01)
*G01N 21/88* (2006.01)
*G01N 21/21* (2006.01)
*G01N 21/956* (2006.01)

(52) U.S. Cl.
CPC ..... *G01N 21/9505* (2013.01); *G01N 21/8806* (2013.01); *G01N 21/9501* (2013.01); *G01N 21/21* (2013.01); *G01N 2021/8845* (2013.01); *G01N 2021/95676* (2013.01); *G01N 2201/061* (2013.01); *G01N 2201/08* (2013.01)

(58) Field of Classification Search
USPC .......... 356/237.1–237.6, 238.3, 239.1–239.8
See application file for complete search history.

(56) References Cited

U.S. PATENT DOCUMENTS 7,351,980 B2 4/2008 Lange
9,075,027 B2 * 7/2015 Lange ................ G01N 21/9501
(Continued)

FOREIGN PATENT DOCUMENTS

JP 2009117691 A 5/2009
KR 20110089506 A 8/2011

OTHER PUBLICATIONS

"U.S. Appl. No. 14/078,271, Ex Parte Quayle Action mailed Dec. 18, 2014", 5 pgs.

(Continued)

*Primary Examiner* — Tri T Ton
(74) *Attorney, Agent, or Firm* — Kwan & Olynick LLP

(57) ABSTRACT

Disclosed are methods and apparatus for inspecting a vertical memory stack. On an inspection tool, incident light having a first wavelength range is used to detect defects on a surface of the vertical memory stack. On the inspection tool, incident light having a second wavelength range is used to detect defects on both the surface and throughout a depth of the vertical memory stack. The defects detected using the first and second wavelength range are compared to detect defects only throughout the depth of the vertical memory stack, excluding defects on the surface, as well as to detect defects only on the surface.

20 Claims, 12 Drawing Sheets

Related U.S. Application Data

(60) Provisional application No. 61/729,329, filed on Nov. 21, 2012.

(56) References Cited

U.S. PATENT DOCUMENTS

| | | |
|---|---|---|
| 2002/0036771 A1 | 3/2002 | Sato et al. |
| 2002/0149782 A1 | 10/2002 | Raymond |
| 2008/0243412 A1 | 10/2008 | Horie et al. |
| 2010/0322000 A1 | 12/2010 | Shim et al. |
| 2013/0017629 A1 | 1/2013 | Pyo et al. |
| 2014/0139830 A1 | 5/2014 | Lange |

OTHER PUBLICATIONS

"U.S. Appl. No. 14/078,271, Notice of Allowance mailed Mar. 3, 2015", 7 pgs.
"International Application Serial No. PCT/US2013/071115, Search Report and Written Opinion mailed Mar. 21, 2014", 9 pgs.
Arya, Pranav, "A Survey of 3D Nand Flash Memory", EECS Int'l Graduate Program, National Chiao Tung University, 11 pgs.
Jang, Jaehoon et al., "Vertical Cell Array using TCAT (Terabit Cell Array Transistor) Technology for Ultra High Density NAND Flash Memory", 2009 Symposium on VLSI Technology Digest of Technical Papers, 2009, pp. 192-193.

\* cited by examiner

APPARATUS AND METHODS FOR DETECTING DEFECTS IN VERTICAL MEMORY

CROSS-REFERENCE TO RELATED APPLICATION

This application is a continuation of and claims the benefit under 35 U.S.C. §120 of U.S. application Ser. No. 14/078,271, entitled APPARATUS AND METHODS FOR DETECTING DEFECTS IN VERTICAL MEMORY, filed 12 Nov. 2013 by Steven R. Lange, which claims priority of U.S. Provisional Patent Application No. 61/729,329, entitled SIMULTANEOUS MULTI-MODE DEFECT INSPECTION FOR 3D WAFERS, filed 21 Nov. 2012 by Steven R. Lange. Both applications are incorporated herein by reference in their entirety for all purposes.

TECHNICAL FIELD OF THE INVENTION

The invention generally relates to the field of wafer and reticle inspection systems. More particularly the present invention relates to inspection of vertical device structures.

BACKGROUND

As demand for ever-shrinking semiconductor devices continues to increase, it has become particularly difficult to continue shrinking semiconductor devices, such as memory, due to rapidly increasing costs associated with lithography and multiple process steps associated with pitch splitting techniques.

Vertical memory, such as 3D or vertical NAND (VNAND) memory, appears to be a promising direction for increasing memory density. Implementation of 3D or VNAND includes building transistors (bits) vertically, rather than orienting memory structures in a planar manner. Early VNAND devices have 16 to 24 vertical bits with future plans to vertically extend to 48 and 64 bits. These changes are achieved with fewer process steps, relaxed lithography sizes, and lower manufacturing costs, as compared with the planar approach.

Various inspection systems are used within the semiconductor industry to detect defects on a semiconductor reticle or wafer. However, there is a demand for improved semiconductor wafer inspection systems for implementation with vertical semiconductor devices, such as 3D or VNAND memory.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method for inspecting a vertical memory stack is disclosed. On an inspection tool, incident light having a first wavelength range is used to detect defects on a surface of the vertical memory stack. On the inspection tool, incident light having a second wavelength range is used to detect defects on both the surface and throughout a depth of the vertical memory stack. The defects detected using the first and second wavelength range are compared to detect defects only throughout the depth of the vertical memory stack, excluding defects on the surface, as well as to detect defects only on the surface.

In a specific implementation, the first wavelength range is a red-visible, ultraviolet and/or a deep ultraviolet range and the second wavelength is a blue-visible, infrared, and/or near infrared range. In a further aspect, the first wavelength range is less than about 450 nm and the second wavelength is equal to or greater than about 0.70 microns, and the vertical memory stack comprises a plurality of poly silicon and oxide layers through which incident light at the second wavelength range penetrates and, in response, output light is scattered or reflected back through the poly silicon and oxide layers to be detected by a detector of the inspection tool. In yet a further aspect, defects are detected in the vertical memory stack prior to forming word-line (W/L) trenches in the plurality of poly silicon and oxide layers.

In another implementation, the vertical memory stack comprises a plurality of tungsten and oxide layers having a trench into which incident light at the second wavelength penetrates into the trench. In a further aspect, the tungsten layers were formed by a process that replaces a plurality of nitride layers. In another example embodiment, the vertical memory stack comprises a plurality of nitride and oxide layers through which incident light at the second wavelength penetrates and, in response, output light is scattered or reflected back through the nitride and oxide layers to be detected by a detector of the inspection tool. In a further aspect, defects are detected in the vertical memory stack prior to forming word-line (W/L) trenches in the plurality of nitride and oxide layers.

In another embodiment, the method includes vertically or horizontally polarizing the incident light that has the second wavelength range. In one embodiment, a trench is formed adjacent to the vertical memory stack and the second wavelength range is selected to result in a maximum intensity of light to reach a plurality of depths within the trench.

In another embodiment, the invention pertains to inspection system for inspecting a vertical semiconductor structure, such as a vertical memory structure. The system includes an illumination optics module for generating and directing an incident beam towards a vertical semiconductor structure at both a first wavelength range that is between 600 and 950 nm and a second wavelength range that is less than about 450 nm. The system further includes a collection optics module for collecting an output beam at the first wavelength range and at the second wavelength range. The output beam is reflected or scattered from the vertical semiconductor structure in response to the incident beam. The system also includes a first detector for detecting the output beam collected at the first wavelength range and a second detector for detecting the output beam collected at the second wavelength range. The system further comprises a controller for (i) detecting defects on a surface of the vertical semiconductor structure based on the detected output beam at the first wavelength range; (ii) detecting defects on both the surface and throughout a depth of the vertical semiconductor structure based on the detected output beam at the second wavelength range; and (iii) comparing the defects detected using the first and second wavelength range to detect defects only throughout the depth of the vertical semiconductor structure, excluding defects on the surface, as well as to detect defects only on the surface. In other embodiments, the controller is configured to perform one or more of the above described operations with respect to any of the above described devices or structures.

In a specific implementation, the illumination module includes an optical element for splitting an illumination beam into a shorter wavelength beam at the first wavelength range that is directed along a shorter band path and a longer wavelength beam at the second wavelength range that is directed along a longer band path. In another aspect, the illumination module further includes a first polarizer in the shorter band path for providing horizontal or vertical polarization in the shorter wavelength beam at the first wavelength range and a second polarizer in the longer band path for providing horizontal or vertical polarization in the longer wavelength beam at the second wavelength range. In another aspect, the illumination module further includes a sub-band filter in the longer band paths for applying across each of the first wavelength range so as to bandpass a sub-band in the first wavelength range that has a width that is equal to or less than about 50 nm. In another embodiment, the optical element for splitting an illumination beam is a dichroic beam splitter for reflecting the incident beam at one of the first and second wavelength ranges and transmitting the incident beam at another one of the first and second wavelength ranges.

In another aspect, the illumination module further includes a second optical element for recombining the longer and shorter wavelength beams for directing towards the vertical semiconductor structure. In a further aspect, the illumination module further includes a third optical element for inserting an autofocus beam at a third wavelength range that differs from the first and second wavelength ranges. In yet another embodiment, the illumination module includes optical elements in the shorter band path that each minimizes color aberrations across the first wavelength range and optical elements in the longer band path that each minimizes color aberrations across the second wavelength range.

These and other aspects of the invention are described further below with reference to the figures.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known component or process operations have not been described in detail to not unnecessarily obscure the present invention. While the invention will be described in conjunction with the specific embodiments, it will be understood that it is not intended to limit the invention to the embodiments.

Although inspection systems and techniques are described herein as being applied to certain types of vertical NAND (VNAND) memory structures, it is understood that embodiments of the present invention may be applied to any suitable 3D or vertical semiconductor structures, such as NAND or NOR memory devices formed using terabit cell array transistors (TCAT), vertical-stacked array transistors (VSAT), bit cost scalable technology (BiCST), piped shaped BiCS technology (P-BiCS), etc. The vertical direction is generally a direction that is perpendicular to the substrate surface. Additionally, although particular fabrication steps, processes, and materials are described for forming such 3D structures, inspection embodiments may be applied at any point in the fabrication flow that results in multiple layers being formed on a substrate, and such layers may include any number and type of materials.

General fabrication techniques for forming vertical structures, such as VNAND, will be described prior to describing various inspection systems and techniques embodiments of the present invention. Specific fabrication details and material types and characteristics are omitted for clarity purposes.

Figure 1A:
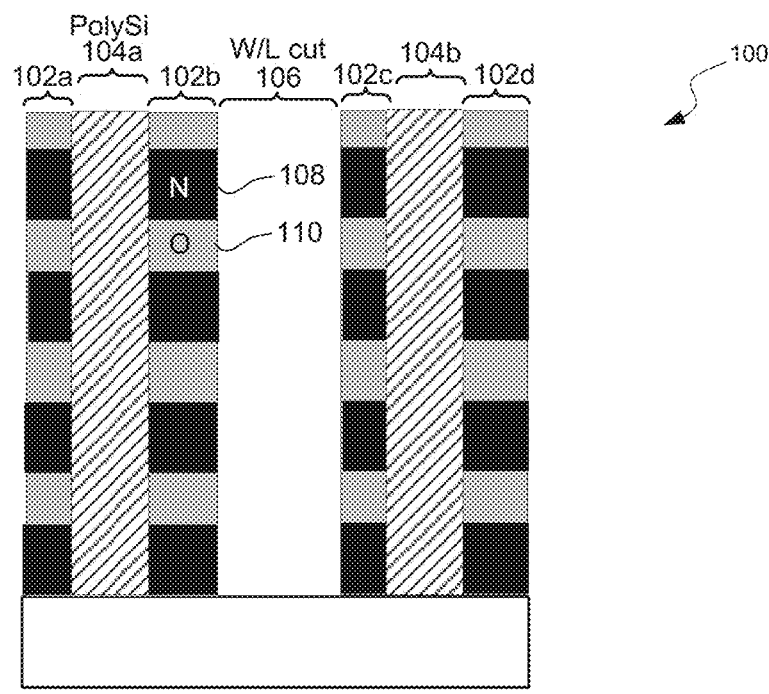
FIGS. 1A-D illustrate a process for fabricating a "gate last" type of vertical NAND (VNAND) memory devices.

FIGS. 1A-D illustrate a process for fabricating a "gate last" type of vertical NAND (VNAND) memory device. This gate last architecture may generally include alternating layers of oxide and SiN or nitride materials, which are collectively referred to as an oxide-nitride-oxide-nitrite (ONON) structure. FIG. 1A is a diagrammatic side view of the patterned ONON layers of a gate last VNAND memory portion 100. As shown, alternating layers of an oxide (O) and nitride (N) material are patterned into ONON stacks 102a, 102b, 102c, and 102d. For instance, stack 102b includes oxide (O) layer portion 110 and nitride (N) layer portion 108. The ONON stacks may be formed by any suitable deposition and etching process so as to form the ONON stacks, as well as the W/L (word-line) cuts (e.g., 106) and vias (e.g., 104a and 104b) for receiving polysilicon (PolySi) material. As shown, polysilicon (PolySi) may also be deposited and etched to fill vias or channels 104a and 104b between sets of ONON stacks.

Figure 1B:
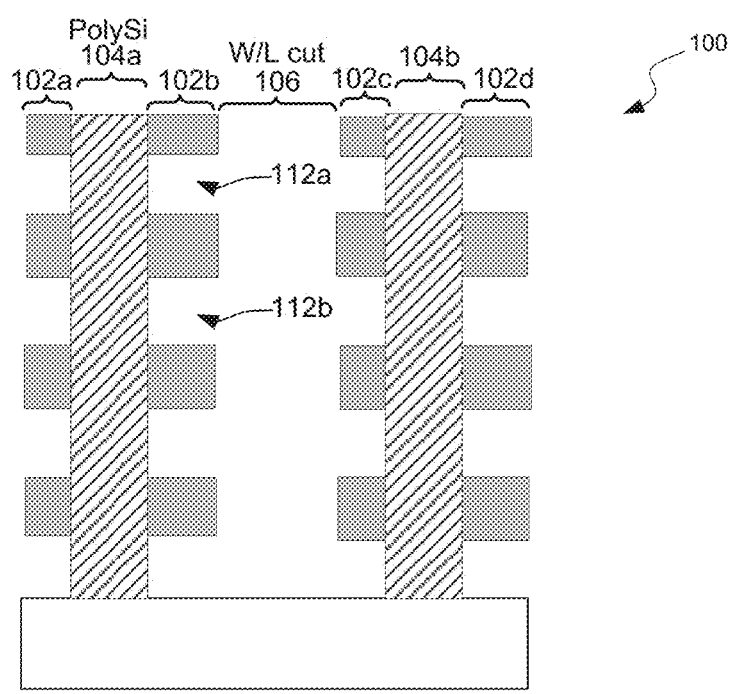
Figure 1C:
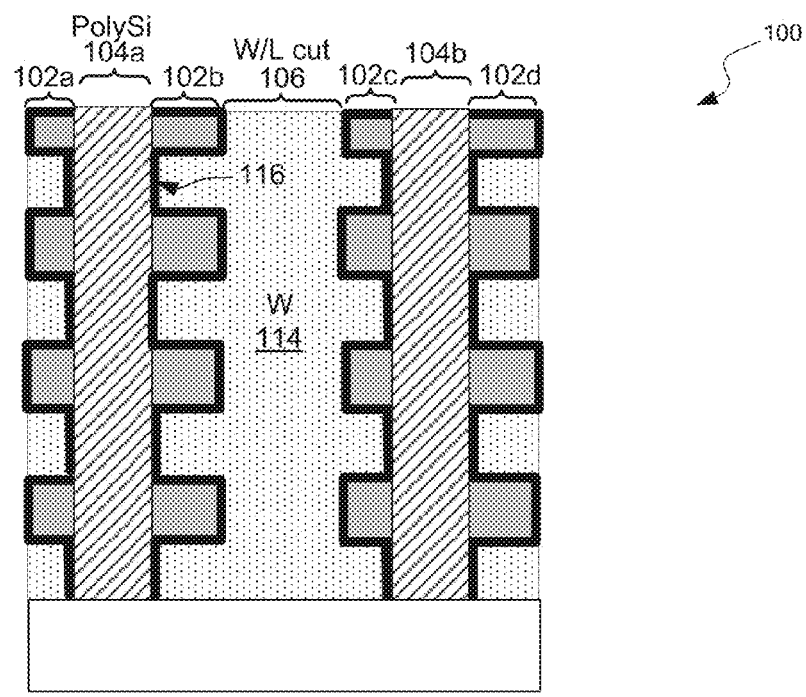
Figure 1D:
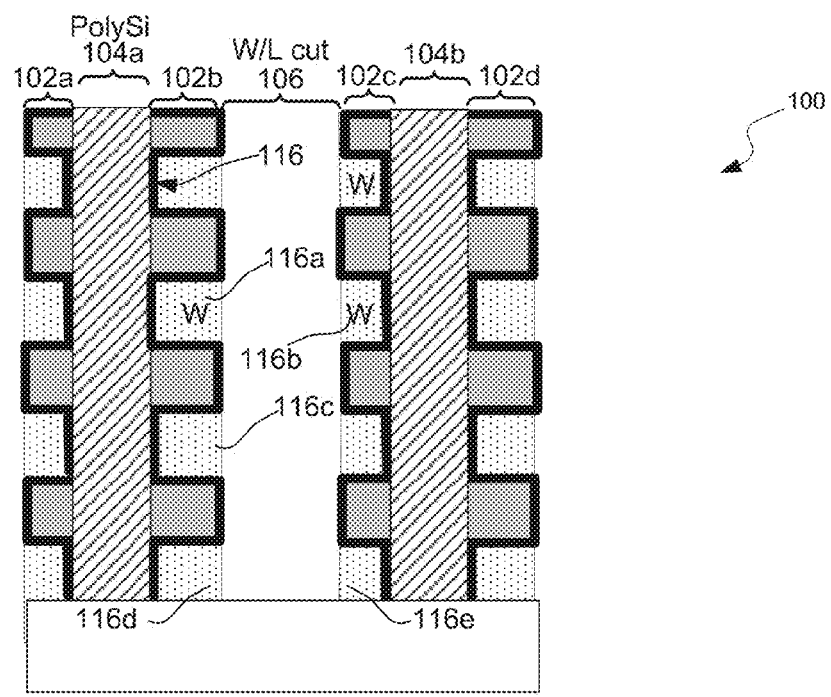

FIG. 1B illustrates the gate last VNAND portion 100 after removal of the nitride material, for example, from areas 112a and 112b. For example, the nitride material may be removed using a wet etch process. FIG. 1C illustrates the VNAND portion 100 after a gate material, e.g., tungsten (W) 114, has been deposited. A dielectric layer 116 is also deposited. The W and dielectric materials are formed within the spaces from which the nitride was previously etched. That is, the nitride material is replaced by the W material. FIG. 1D shows the VNAND portion 100 after the W material is etched back so as to form isolated gate portions, such as 116a, 116b, 116c, 116d, and 116e.

Vertical memory devices tend to have thicker stacks of materials and structures, as compared with planar memory devices. For instance, early VNAND devices have 2-3 µm thick stacks, and future stacks are predicted to be in the 6-8 µm range. Some stacks can easily include 60 to 90 layers at varying thicknesses. In comparison, a typical planar memory thickness is about 0.1 to 1 µm, depending upon the process step.

Figure 1E:
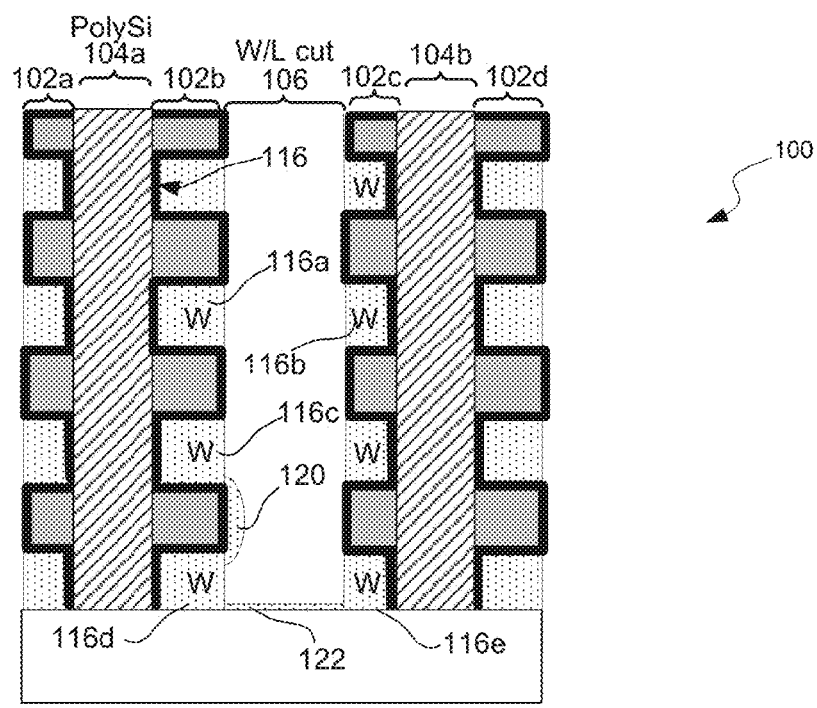
FIG. 1E illustrates the VNAND structure portion of FIG. 1D with defects present in its stack.

Defects in the processing steps can occur throughout these stacks and need to be detected and separated from surface defects, their source identified, and corrected to ensure high manufacturing yields. FIG. 1E illustrates the VNAND structure portion 100 of FIG. 1D with defects present in its stack. As shown, a W bridge 120 is formed between gate portions 116c and 116d, while another bridge 122 is formed between gate portions 116d and 116e. It may also be possible to have a void within an oxide portion so that there is a short between two W portions that are designed to be isolated from each other, leftover nitride material, etc.

Figure 1F:
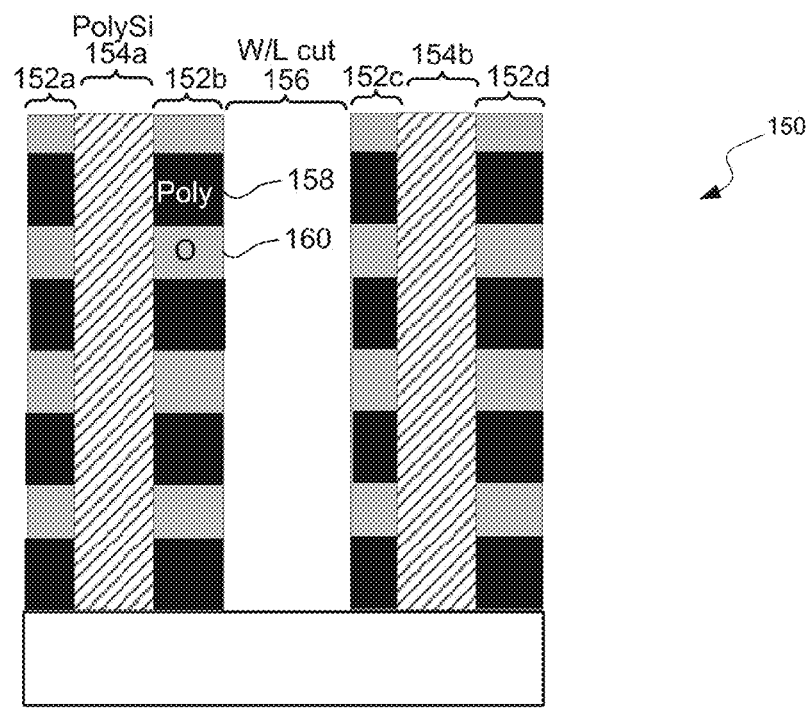
FIG. 1F is a diagrammatic side view of a gate first type of VNAND structure.

FIG. 1F is a diagrammatic side view of a gate first type of VNAND structure. As shown, a gate first VNAND portion may be formed by depositing alternating oxide (O) and poly silicon (Poly Si) layers, which are patterned into stacks 152a, 152b, 152c, and 152d. For example, stack 152b includes poly silicon (poly) gate portion 158 and oxide (O) portion 160. This type of VNAND is referred to as a OPOP VNAND memory device. The VNAND portion 150 may also include Poly Si channels (or other channel materials) 154a and 154b, as well as W/L cut area 156. Defects may be present at any of the levels of the OPOP structure. For instance, extra material or voids may be present in any of the layers of an OPOP structure.

Regardless of the particular type of fabrication process, defects need to be detected in all levels of a multiple layer stack and as early as possible in the particular process. However, the different types of vertical structures at various fabrication stages may require different inspections for detecting defects within the stack. For instance, surface defects may be generally detected with shorter wavelengths, while other types of stacks are difficult to inspect at shorter wavelengths.

Certain inspection embodiments preferably include detection of defects throughout a stack, including the stack surface and throughout the various depths of a stack. For example, certain embodiments allow defects to be found at depths of up to about 3 µm. In another embodiment, defects can be detected at stacks depths that are as large as about 8 µm. Transmission through an ONON or OPOP stack is not limited by absorption at the longer wavelengths, so there is no real limit to the thickness of the vertical ONON or OPOP stack that can be theoretically inspected.

An OPOP structure may be difficult to penetrate with shorter wavelengths during an inspection process. Poly Si is quite opaque for wavelengths below 450 nm and gradually becomes more transparent at longer wavelengths. Poly Si becomes completely transparent at about 1.06 um. During inspection, light ideally needs to have long enough wavelengths penetrate the stack of Poly Si and reach a particular defect location and result in light scattered from the defect being able to penetrate back through the stack of Poly Si to be detected. In sum, longer wavelengths can be used to reach and detect defects that are located deep within an OPOP stack.

For an ONON stack, on the other hand, all of the materials are transparent above about 240 nm. However, later on in the fabrication process, the SiN is replaced by Tungsten, which is opaque to all wavelengths. However, light at longer wavelengths (greater than about 600 or 700 nm) can penetrate to about 1 um depth into a trench within a tungsten and oxide stack if the light is polarized in a direction perpendicular to the trench. Thus, longer wavelengths and certain polarization settings can be used to inspect the ONON layers after the Tungsten replacement occurs to see defects in the stack.

Figure 2:
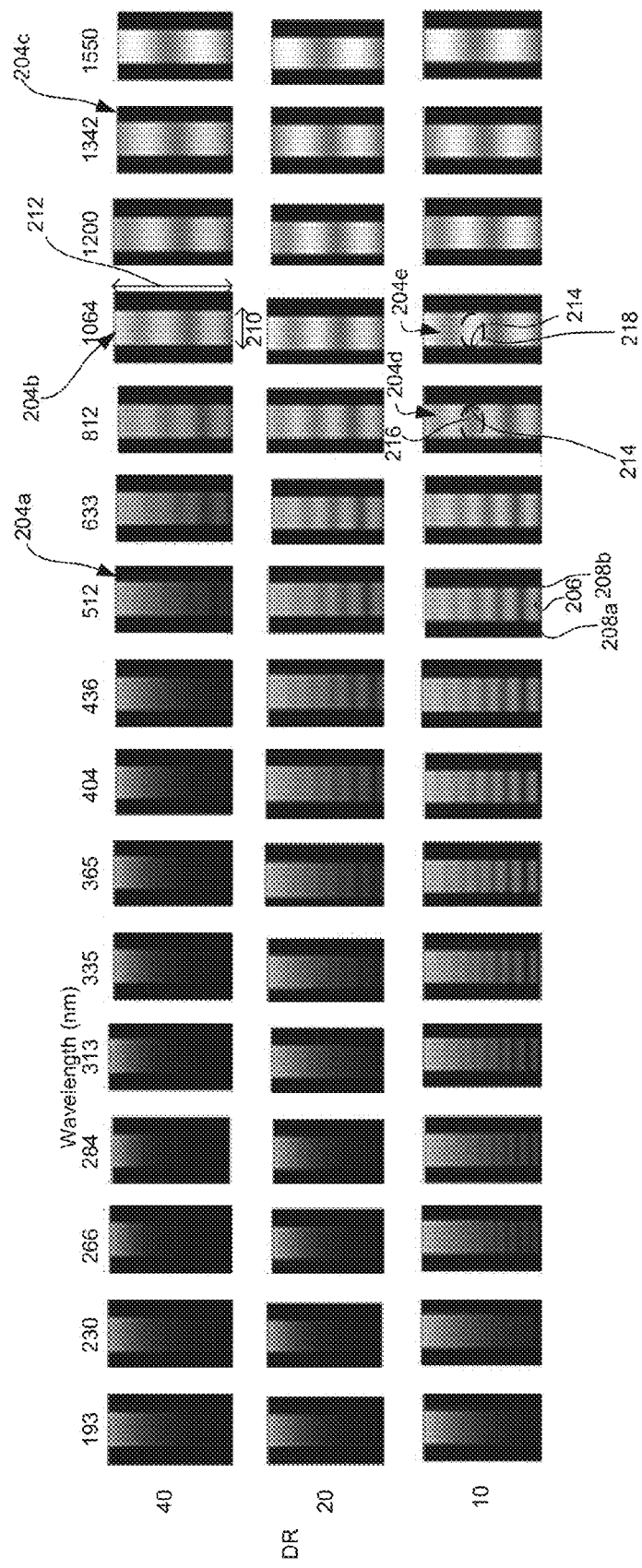
FIG. 2 shows electric field penetration into a Tungsten trench that is 1 um thick as a function of wavelength for polarization that is perpendicular to the trench.

FIG. 2 shows electric field (e-field) penetration into a Tungsten slot that is 1 um thick as a function of wavelength for polarization that is perpendicular to the trench. A plurality of simulated e-field images (e.g., 204a, 204b, 204c, 204d, and 204e) are shown at different wavelengths and different design rules (DR). Each e-field image corresponds to a trench having a 1 um depth (e.g., 212) and a width (e.g., 210). Each image includes dark side walls (e.g., 208a and 208b) having no e-field penetration and different e-field intensities at different positions within the trench using different wavelengths. For instance, the white portions of the trench image portions correspond to depth positions in the trench at which the e-field is strong and can optimally detect defects, while the darker portions correspond to weaker e-field at particular depths of the trench.

Each column of images corresponds to a different wavelength, starting at 193 nm for the leftmost column of images and going to 1550 nm for the rightmost column of images. Each row represents a different design rule (DR) having values 40 nm, 20 nm, and 10 nm for the top row, middle row, and bottom row, respectively.

E-field penetration of the trench seems to dramatically improve at the longer wavelengths. That is, longer wavelengths penetrate to the bottom of the trench. One goal is to concentrate the light's electric field at various levels of the trench and stack to detect defects at multiple levels of the stack. Additionally, different patterns of e-field penetration occur at different trench depth positions for different wavelengths. This effect is shown as different bands of light and dark intensity in the trench for each wavelength. For example, e-field image 204d for a wavelength of 812 nm has weak e-field penetration at trench position 214, which is shown as a low intensity black band 216, of a 10 nm DR trench, while e-field image 204e for a wavelength of 1064 nm shows strong e-field penetration at this same position 214, which is shown as a high intensity white band 218. Thus, a wavelength of 1064 nm may be used to more effectively detect defects at position 214 of a 10 nm DR trench. A range of long wavelengths would be selected to detect defects at a wide range of trench depths (e.g., up to 950 nm).

Figure 3B:
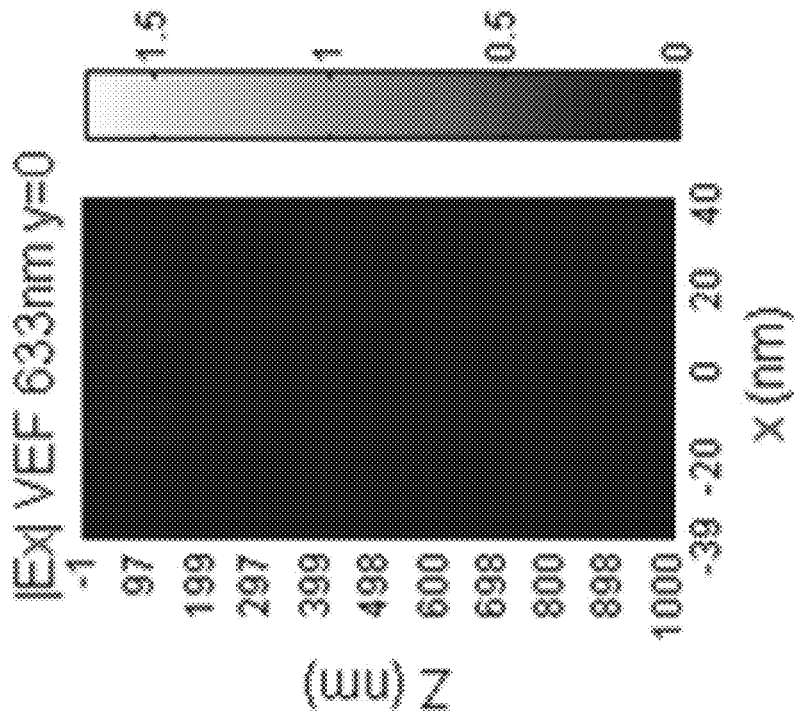
FIGS. 3A and 3B illustrate a comparison between horizontal and vertical polarization, respectively, for a 1 um tungsten trench.
Figure 3A:
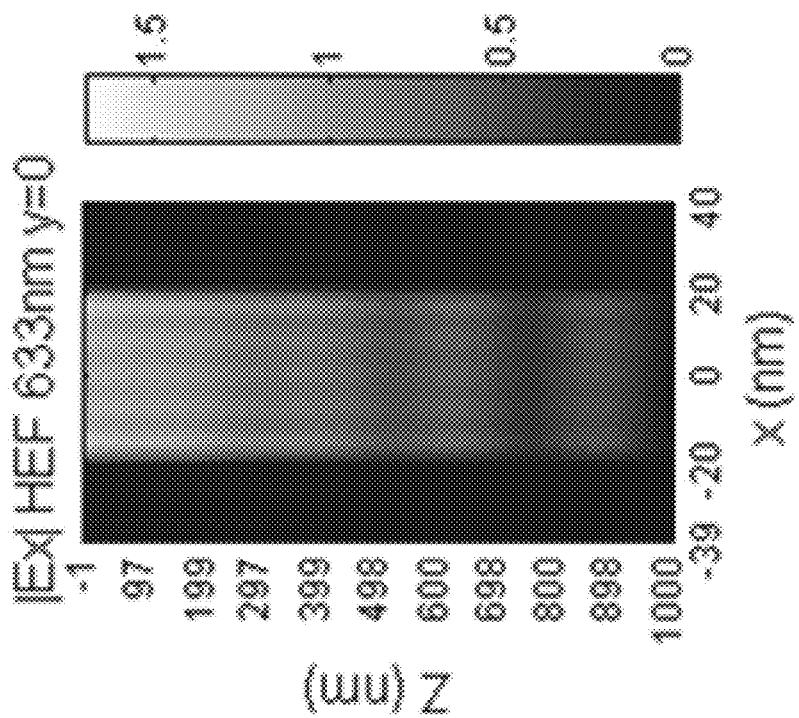

FIGS. 3A and 3B illustrate a comparison between horizontal and vertical polarization, respectively, for a 1 um tungsten slot. A horizontal polarization is perpendicular to the trench, while a vertical polarization is parallel to the trench. At a wavelength of 633 nm and a horizontal polarization (HEF, the e-field penetrates the trench as shown in FIG. 3A. In contrast, there is no e-field penetration at the same 633 nm wavelength for vertical polarization (VEF) as shown in FIG. 3B.

Figure 4A:
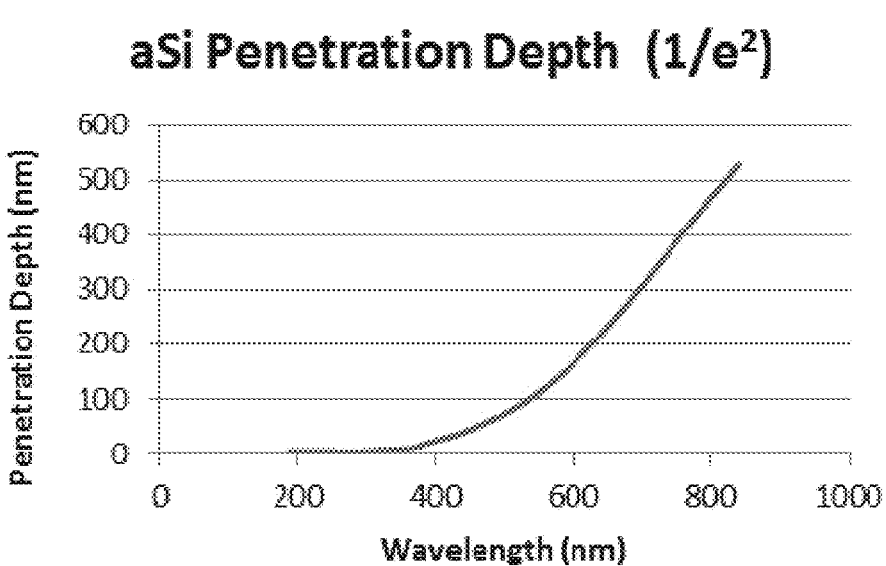
FIG. 4A shows amorphous Si penetration depth as a function of wavelength.

In sum, the penetration depth of various absorbing materials varies with wavelength, with more penetration at longer wavelengths. FIG. 4A shows amorphous Si penetration depth as a function of wavelength. If only a wavelength of 600 nm were chosen, the light will penetrate to a depth of about 160 nm. One can then use different wavelengths to penetrate more or less into the material. Thus, if one uses multiple inspections at longer and longer wavelengths, these longer wavelengths will be sensitive to defects at deeper and deeper depths. As a result, inspections as a function of wavelength corresponds to inspecting at different depths in the wafer stack as a function of wavelength. Wavelengths below about 450 nm will not penetrate such a stack and will only be sensitive to defects above the absorbing material.

Figure 4B:
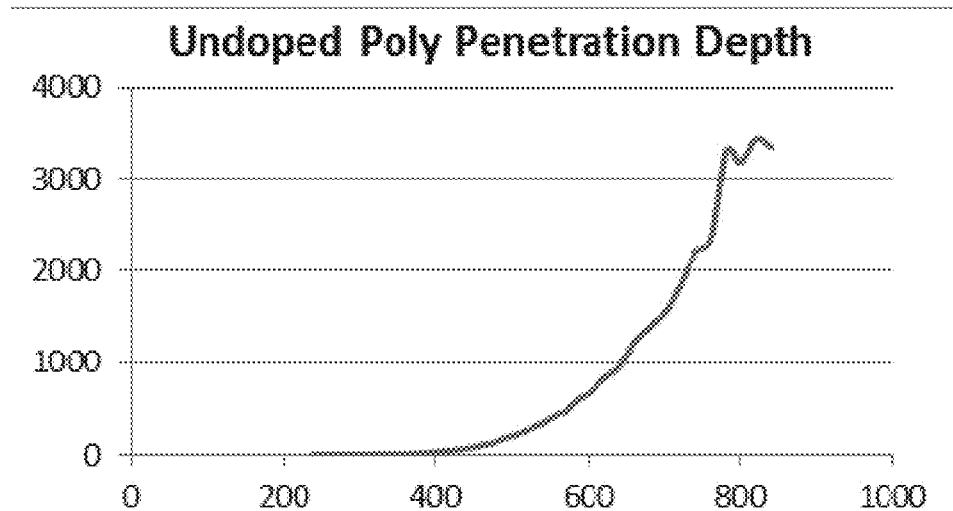
FIG. 4B shows the penetration depth for undoped Poly Silicon.

FIG. 4B shows the penetration depth for undoped Poly Si, with again similar depth penetration vs. wavelength characteristics. Certain embodiments of the invention can use multiple wavebands to view into different depths of the Poly Si (e.g., of an OPOP structure), as well as other types of stacks. The OPOP layers can be inspected prior to formation of other structures, such as the W/L trenches, of the VNAND device, as well as after formation of other structures, such as the W/L trenches.

Figure 5:
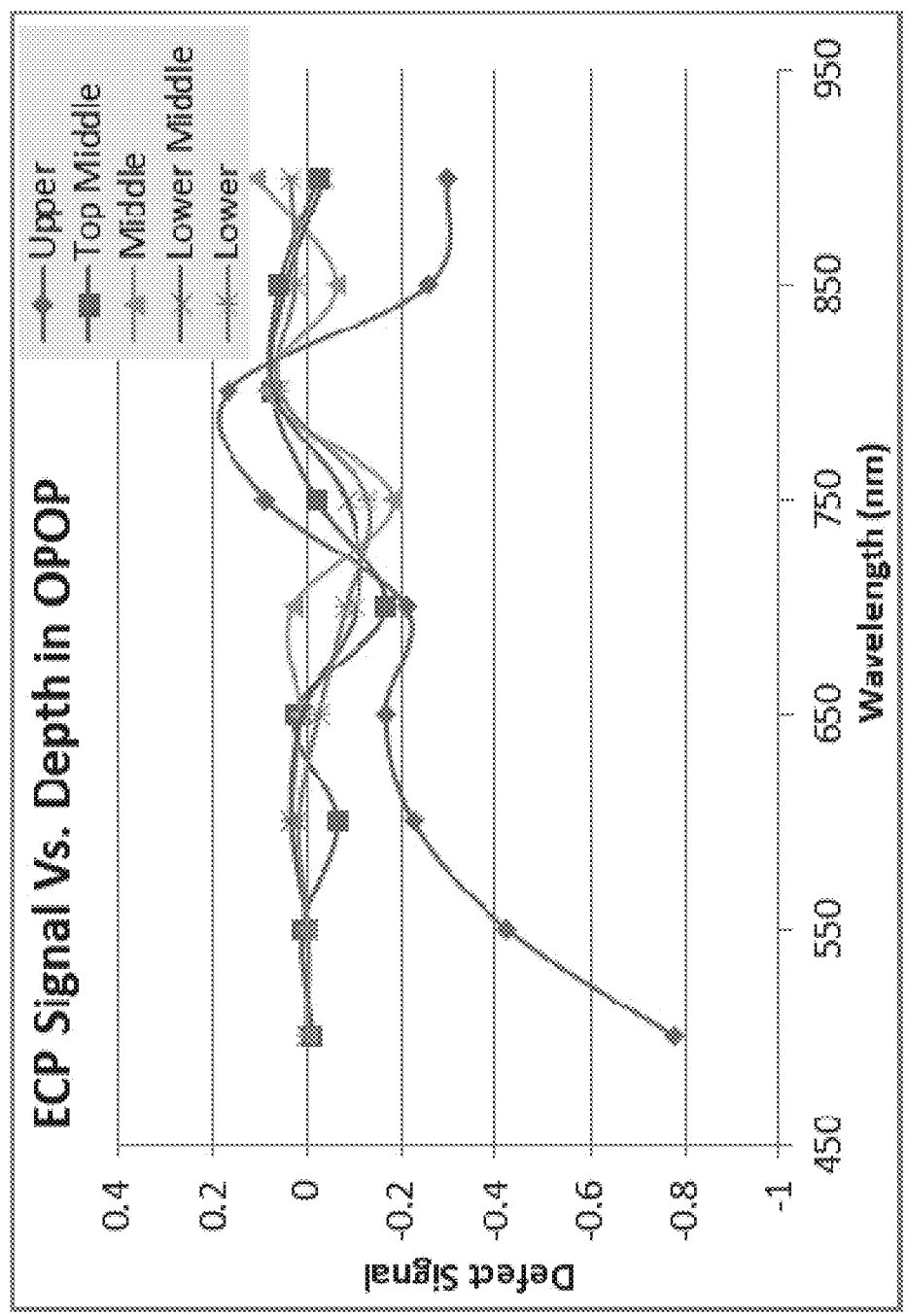
FIG. 5 illustrates simulated defect signals as a function of depth for an OPOP deposition with a particle positioned at various depths.

A defect signal can vary significantly over various wavelength ranges and depth positions. FIG. 5 illustrates simulated defect signals as a function of depth for an OPOP deposition with a particle positioned at various depths. For the particle that was the highest in the OPOP stack ("Upper"), the signals at wavelengths between about 500 nm and 900 nm are generally strong, with even the 500 nm wavelength having a good signal. As the depth of the particle increases (from "Top Middle" to "Lower"), the signals decrease for the shorter wavelengths and remain stronger at the longer wavelengths. That is, Poly Si typically is opaque to shorter wavelengths, and more transparent to longer wavelengths. Thus, longer wavelengths would result in more signal penetration for an OPOP structure. Longer wavelengths may be chosen to penetration OPOP stacks, especially before trenches are formed. The wavelength range is selected so that the incident light penetrates to the bottom of the OPOP stack and then is returned in the form of reflected or scattered light from the bottom of the stack and out through the surface of such stack.

Tungsten (W) is also opaque at shorter wavelengths. However, longer wavelengths can be selected to inspect ONON type stacks after the nitride has been replaced with W because these longer wavelengths can penetrate the W-separation slot. Even for materials that are relatively transparent to shorter wavelengths, such as an ONON structures, longer wavelengths tend to result in a stronger detection signal.

The detected signal for a particular defect can also oscillate significantly, depending on the wavelength value. The signal oscillates with wavelength due to the changing of the standing wave effect, where wavelength changes the standing nodes causing the signal to vary. If broadband light or a large wavelength range were used, the signal for a defect may average out to zero. Additionally, certain wavelengths may result in a null signal value for a defect. Thus, narrow bandwidth ranges for both surface defect detection and deep defect detection can be selected so as to result in stronger and more stable defect detection signals. For instance, a longer range of wavelengths is selected to have no more than a 50 nm width.

Any suitable inspection system may be implemented for inspecting at two different wavelength ranges to detect defects on the surface and at various depths of a multiple layer semiconductor stack, such as a VNAND structure. In general, an inspection tool may include at least one light source for generating an incident light beam at different wavelengths to detect defects on a surface and at various depths of a vertical semiconductor stack, illumination optics for directing the incident beam to the stack, collection optics for directing an output beam that is emitted from the stack in response to the incident beam, a sensor for detecting an output beam and generating an image or signal for the output beam, and a controller for controlling the components of the inspection tool and facilitating detect detection on the surface and at various depths in the stack as described further herein.

In one embodiment, an inspection tool includes illumination and collection modules for generating and collecting light at longer wavelengths (700-950 nm) and simultaneous shorter wavelengths (190-450 nm). In a specific embodiment, the inspection tool generates and collects light in two wavelength ranges: a near infrared (NIR) or IR range and a shorter visible to deep ultraviolet (DUV) (or UV) range. The shorter wavelength range may be used for detection of surface defects, while the longer wavelengths may be used to detect deeper defects in a thick stack, for example. The inspector tool may also provide polarization options for parallel and perpendicular e-field and a set of sub-band wavelength filters for applying across the wavelength range for each of the long and short wavelength paths.

Use of simultaneous short and long wavelengths allow the capture of (i) the surface defects with shorter wavelengths, (ii) both surface and defects buried in the stack by the use of the longer wavelengths, and (iii) only the buried defects by using a difference of the shorter and longer wavelength defect reports.

Figure 6:
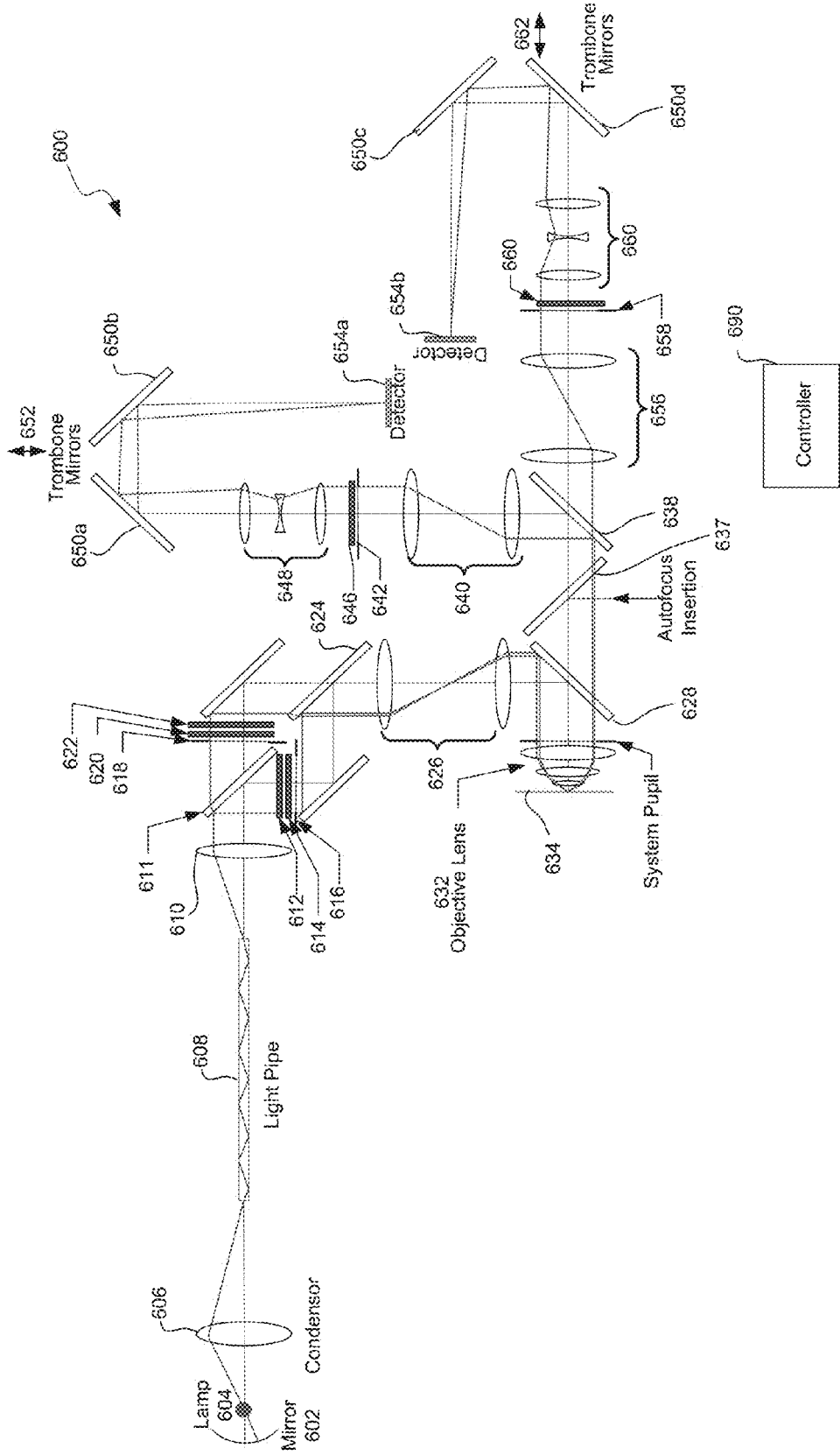
FIG. 6 is a diagrammatic representation of an example inspection apparatus in accordance with a specific implementation of the present invention.

FIG. 6 is a diagrammatic representation of an example inspection system 600 in accordance with a specific implementation of the present invention. As shown, the system 600 includes a broadband light source (e.g., Xe arc lamp 604) which is directed and focused via mirror 602 and condensor lens 606 into light pipe 608. The light pipe generally homogenizes light. The homogenized light may then be received by lens 610, which collimates the received light.

Examples of light sources include a laser-driven light source, a high-power plasma light source, a transillumination light source (e.g., halogen or Xe lamp), a filtered lamp, LED light sources, etc. The inspection system may include any suitable number and type of additional light sources, besides broadband light sources.

The system 600 also includes optical elements for splitting the incident beam into a shorter wavelength beam that is directed along a shorter band path and a longer wavelength beam that is directed along a longer band path. As shown, the system 600 includes a dichroic beam splitter 611 for splitting the incident light into two different wavelength band paths. In the illustrated system, a first wavelength path includes a first spectral filter 620 and first polarizer 622 positioned near a first illumination pupil 618. The second wavelength path includes a second spectral filter 614 and second polarizer 612 positioned near a second illumination pupil 616.

A dichroic beam splitter or filter may be implemented in any suitable manner. For instance, dichroic prisms with dichroic optical coatings, which selectively reflect or transmit light depending on the light's wavelength, may be utilized in the system 600 to separate the incident beam into two separate wavelength paths.

A pupil that is conjugate to the system pupil (located at the objective lens) may be used in each wavelength path. Each pupil or aperture can have a specific shape to obscure parts of the light path to maximize the signal for that particular wavelength range.

Each spectral filter in each path spectrum may be used to further define the spectrum of each beam. For example, each spectral filter can further be used to optimize the sensitivity of each path for the defects that are intended to be captured. A separate polarizing filter can also be positioned in each spectral path to further optimize the inspection sensitivity for each wavelength range. For example, horizontal polarization (as well as longer wavelengths) may be selected for penetration into vertical trenches of thick stacks.

Figure 7:
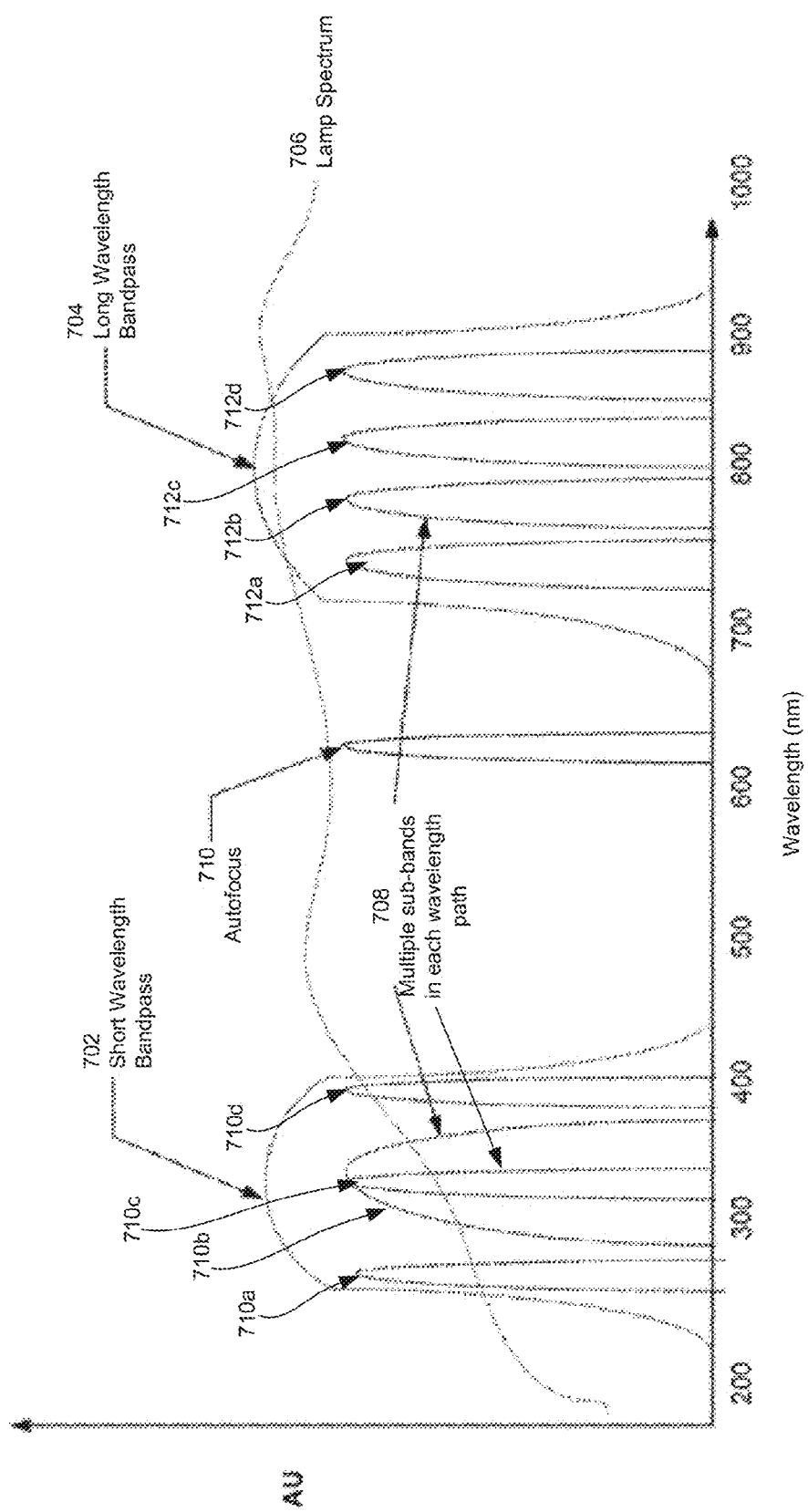
FIG. 7 illustrates selection of longer and shorter wavelength band path spectra from a broadband spectrum for inspection of a multiple layer stack, such as a VNAND structure, in accordance with one embodiment of the present invention.

The selected shorter and longer wavelength ranges for the two paths may be selected in any suitable manner, depending on the particular structure being inspected. FIG. 7 illustrates selection of longer and shorter wavelength band path spectra from a broadband spectrum for inspection of a multiple layer stack, such as a VNAND structure in accordance with one embodiment of the present invention. As shown, a short wavelength bandpass 702 and a long wavelength bandpass 704 may be applied to the lamp broadband spectrum 706 (or any other suitable broadband light generated by one or more light sources).

Figure 8:
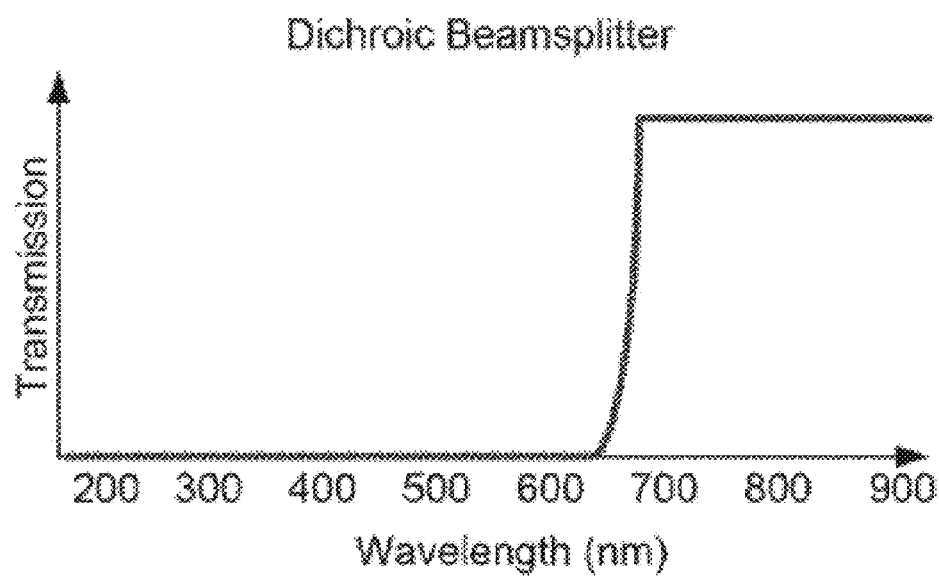
FIG. 8 is a graph of a longer wavelength range being bandpass filtered by the dichroic beam splitter of the system of FIG. 6 in accordance with a specific implementation of the present invention.

In the system of FIG. 6, dichroic beam splitter 611 may be designed to separate the paths into a shorter wavelength range, which is reflected, and a longer wavelength range, which is transmitted as shown in FIG. 8. The shorter wavelength range may have a maximum that is equal or less than about 450 nm to minimize penetration into the poly and Si materials. The minimum value of the short wavelength is optional, depending upon the nature of the inspector system and costs.

Referring back to FIG. 7, sub-bandpass filters can be used in each of the long and short wavelength paths to select particular ones of multiple sub-bands 708 so as to optimize inspection sensitivity. As shown, a first sub-bandpass filter may select one of short sub-bands 710a, 710b, 710c, or 710d, while a second sub-bandpass filter may select one of long sub-bands 712a, 712b, 712c, or 712d. In one implementation, the selected short and/or long sub-band has a width that is equal to or less than about 50 nm.

Generally, each inspection wavelength range may be selected based on optimization of its sub-band, illumination and collection pupil aperture shapes, polarization of the incident and collection path, magnification, pixel size, or any combination thereof.

Each incident beam from the light source may also pass through a number of lenses which serve to relay (e.g., shape, focus or adjust focus offset, filter/select wavelengths, filter/select polarization states, resize, magnify, reduce distortion, etc.) the beam towards a sample. In the illustrated embodiment, the incident beams from the two wavelength paths are directed by illumination path optical elements, such as mirrors, and received by a dichroic beam splitter 624, which is arranged to recombine the incident beams from the two wavelength band paths. The recombined incident beam may then be directed by any illumination optics, such as pupil relay 626, a 50-50 beam splitter 628, and objective lens 632, onto a multiple layer stack on the sample 634.

A pupil relay 626 may be used to reimage the combined light and focus each pupil onto the system pupil at the objective lens 632. A 50-50 beam splitter 628 may be used to send the light to the objective lens 632. The 50-50 beam splitter 628 may also be arranged to send light reflected or scattered from the sample toward the collection optics.

The objective lens 632 is preferably optimized for all of the wavelengths that are used for defect detection. For instance, the objective 632 has a composition, including lens coatings, and arrangement for correction of color aberration. In an alternative embodiment, the objective lens 632 may be an all reflective objective or refractive or a combination (catadioptric) configuration.

The resulting output beam reflected or scattered from the sample may then be received by another dichroic beam splitter 637, which may be arranged to insert an autofocus into the objective lens 632. The autofocus beam may have a wavelength that is separated from the two inspection bands as shown in FIG. 7 (e.g., autofocus has a wavelength 710, which is about 630 nm). The wavelength for the autofocus can be varied as long as it is not in the inspection wavebands for either the short or long wavelength paths, and it does not necessarily need to be in between the inspection bands. Cost and availability of components can affect where the autofocut insertion is located.

Figure 9:
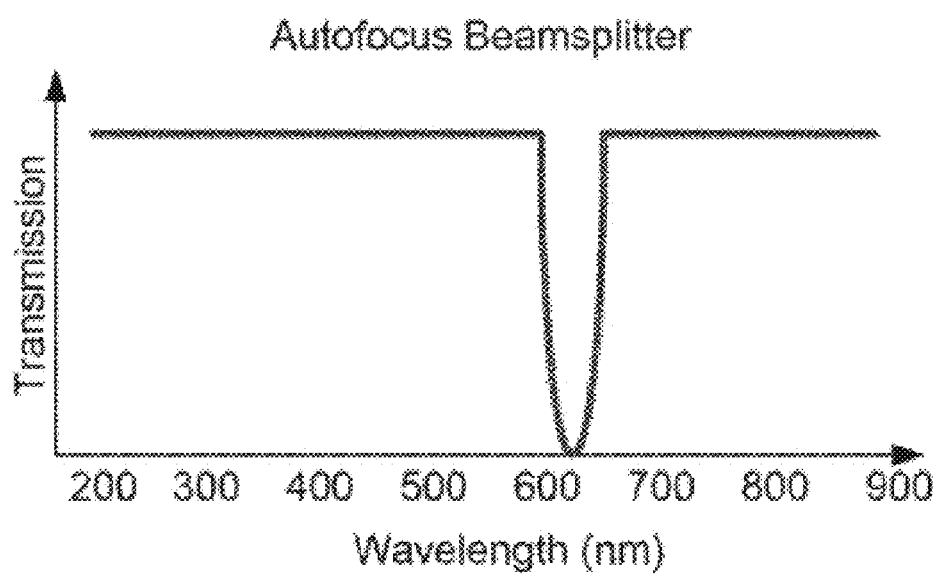
FIG. 9 is a graph illustrating the dichroic beam splitter of FIG. 6 transmitting wavelengths above and below the autofocus wavelength in accordance with one embodiment.
Figure 10:
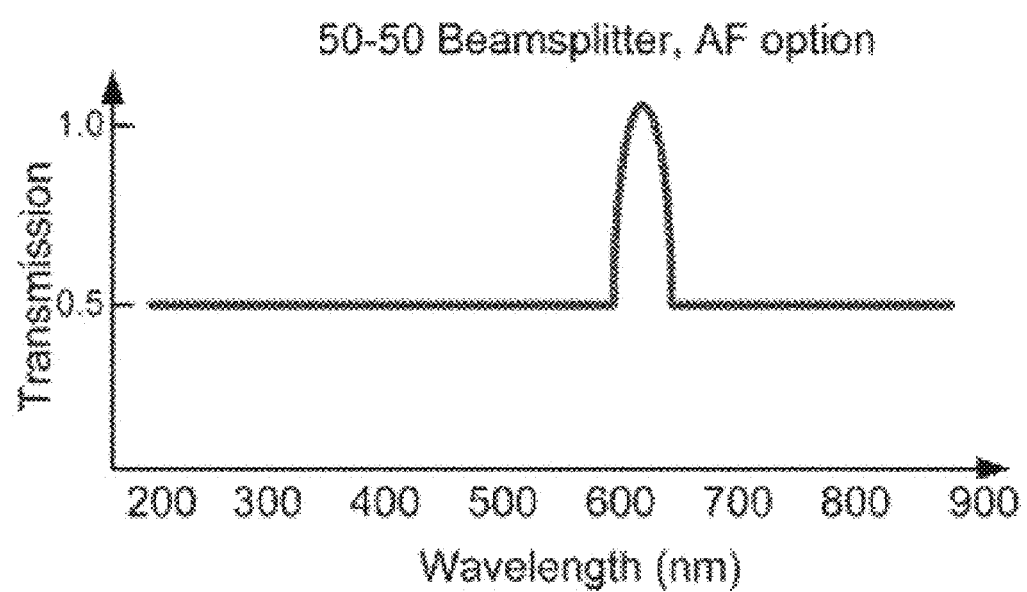
FIG. 10 is a graph of the autofocus wavelength being efficiently bandpass filtered by the 50-50 beam splitter of FIG. 6 in accordance with a specific implementation of the present invention.

In one embodiment, the longer wavelengths may be above the autofocus wavelength and the shorter wavelength range may be below the autofocus bandpass wavelength. The dichroic beam splitter 637 may be arranged to reflect the autofocus waveband and transmit all light above and below that region as shown in FIG. 9. The 50-50 beam splitter 628 can also be configured to pass the autofocus light with high efficiency (e.g., by use of a coating) as shown in FIG. 10. This element may improve the light efficiency of the autofocus by nearly 4×.

The dichroic beam splitter 637 may also be arranged to transmit the reflected or scattered output beam to another output dichroic beam splitter 638, which splits the output beam into longer and shorter wavelength band paths similar to the imaging wavelength bands.

The first output beam may be directed and shaped by any suitable number and type of collection optics, such as pupil relay and magnification lens 640, a polarizer 646 near pupil 642, zoom lens 648, and trombone mirrors 650a and 650b that are independently movable along direction 652. The first output beam is received by a first detector 654a. Likewise, the second output beam may be directed and shaped by any suitable number and type of collection optics, such as pupil relay and magnification lens 656, a polarizer 660 near pupil 658, zoom lens 660, and trombone mirrors 650c and 650d that are independently movable along direction 662. The second output beam is received by a second detector 654b. By way of example, each detector may be in the form of a CCD (charge coupled device) or TDI (time delay integration) detector, photomultiplier tube (PMT), or other sensor.

Each pupil relay 640 and 656 may be designed to form an image of the system pupil (at the objective lens 632) for the purpose of inserting specific apertures in their respective wavelength collection paths so as to optimize the inspection sensitivity for each wavelength. Different aperture setting may be selected so as to achieve different angles of incidence on the sample. A polarizing filter may be positioned in each wavelength path for the purpose of also optimizing the inspection sensitivity. The zoom lenses 648 and 660 2-mirror optical trombones 650a-d may be used to direct the light to separate detectors at different magnifications.

For inspection of VNAND stacks, the long wavelength band pass may be between about 700 nm and 950 nm and the short wavelength may be less than about 450 nm. Sub-band spectral filters (e.g., 614 and 620) can be used in each wavelength path to optimize the inspection sensitivity for either the buried VNAND defects in the long wavelength path or for surface defects, such as particles, in the short wavelength path.

Separate pixel sizes (magnification) can be employed in each path, although the overall scanning of the sample under the inspector can only run at a single speed. In other words, the inspection speed may be dictated by the speed of the detector for the highest magnification, and the lower magnification path will have to run at a reduced speed compared with a speed that may have been possible without the second simultaneous path.

In general, each optical element is optimized for the particular wavelength range of the light in the path of such optical element. For instance, optical elements in the shorter wavelength path are optimized for such shorter wavelength range, while optical elements in the longer wavelength range path are optimized for such longer wavelength range. Likewise, optical elements that are in the path of a combined shorter and longer wavelength range light are optimized for such combined wavelength ranges. Optimization may include minimizing wavelength-dependent aberrations, for example, by selection of glass type, arrangement, shapes, and coatings (e.g., anti-reflective coatings, highly reflective coatings) for minimizing aberrations for the corresponding wavelength range. For example, the lenses are arranged to minimize the effects caused by dispersion by shorter and longer wavelength ranges (both a range between DUV and UV and a range between visible and NIR). In another embodiment, all the optical elements are reflective. Examples of reflective inspection systems and configurations are further described in U.S. Pat. No. 7,351,980 issued 1 Apr. 2008, which patent is incorporated herein by reference in its entirety.

The optical layout of the inspection tool can vary from that described above with respect to FIG. 6. For example, the system microscope objective lens can be one of many possible layouts, as long as the transmission coatings are optimized for the particular selected wavelength band or sub-band and the aberration over each waveband is minimized. Different light sources can be used for each path. For instance, a Xe source may be used for the long wavelength path and an HgXe or Hg lamp may be used for the short wavelength path. Multiple LED or speckle buster laser diodes are also possible sources for each path. The zoom can be modified to include different magnification ranges either via a lens-only approach, a mostly fixed lens with an optical trombone, or any combination thereof.

Certain embodiments of the present invention provide an inspection system that generates light paths simultaneously in both NIR and DUV-to-visible wavelengths. The system may also include components for optional polarized light in each illumination and collection path, optional spectral sub-band filters, and optional aperture shapes in the illumination and collection paths for the inspection of 3D wafer structures.

Certain inspection system embodiments are especially suitable for inspecting semiconductor stack structures, such as 3D or VNAND memory structures. Other types of stack structures that may be inspected or imaged using the inspection apparatus of the present invention include solar panel structures, optical disks, etc.

Figure 11:
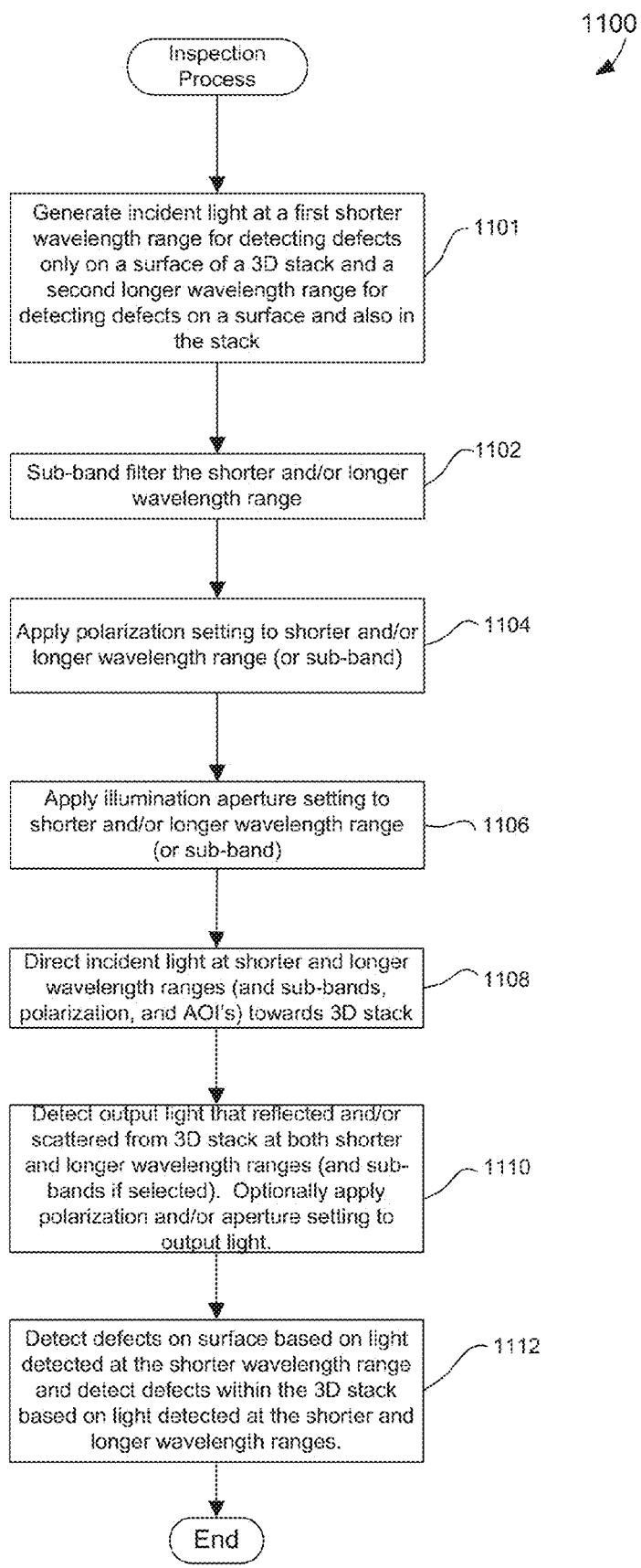
FIG. 11 is a flow chart illustrating a procedure for inspecting a 3D semiconductor structure, such as a VNAND structure, in accordance with a specific implementation of the present invention.

Inspection of defects in 3D semiconductor structures or stacks may be accomplished in any suitable manner. FIG. 11 is a flow chart illustrating a procedure 1100 for inspecting a 3D semiconductor structure, such as a VNAND structure, in accordance with a specific implementation of the present invention. Initially, incident light may be generated at a first shorter wavelength range for detecting defects only on a surface of a 3D stack and a second longer wavelength range for detecting defects on a surface and also in the 3D stack in operation 1101. For instance, VNAND structures are inspected using NIR light to see defects on the top surface and also in the layer stack structure, and these same VNAND structures are also inspected using visible-to-DUV light simultaneously to defect surface defects only.

The shorter and/or longer wavelength ranges may also be sub-band filtered in operation 1102. For instance, light in the longer or shorter wavelength range may be further filtered to select a narrow sub-band having a width that is equal to or less than 50 nm. A polarization setting may also be applied to the longer or shorter wavelength range (or sub-band) in operation 1104. For instance, a horizontal polarization may be selected for the selected longer wavelength sub-band. A polarization setting may be applied based on any suitable inspection parameter, such as defect type, sample composition, wavelength range or sub-band selection, etc.

An aperture setting may also be applied to the shorter and/or longer wavelength range (or sub-band) in operation 1106. For instance, an aperture setting for achieving a particular set of angles of incidence (AOI's) may be selected based any suitable inspection parameter, such as defect type, sample composition, polarization setting, wavelength range or sub-band selection, etc. The incident light at the shorter and longer wavelength ranges (and selected sub-bands, polarization, and AOI's) may then be directed towards the 3D stack in operation 1108.

Output light that is reflected and/or scattered from the 3D stack may then be detected at both shorter and longer wavelength ranges (and sub-bands if selected) in operation 1110. Polarization and aperture setting may also be applied to the collected light. Defects may then be detected on the surface based on light detected at the shorter wavelength range (and sub-band) and defects may be detected within the 3D stack based on light detected at the shorter and longer wavelength ranges (and sub-band) in operation 1112. For instance, the defects within the 3D stack may be determined by subtracting the defects detected at the shorter wavelength range (and sub-band) from the defects detected at the longer wavelength range (and sub-band).

Separation of the surface defects from the subsurface from the simultaneous inspections can be done by observing the spatial coordinates of defects that are common to both inspections. Any defects that have the same spatial location are presumed to be surface defects from the short-wavelength inspection and can be subtracted from the defect list from the long-wavelength inspection.

Referring back to the system of FIG. 6, the system may also include a controller or computer system 690. For instance, the signals captured by each detector can be processed by controller 690, which may include a signal processing device having an analog-to-digital converter configured to convert analog signals from each sensor into digital signals for processing. The controller 690 may be configured to analyze intensity, phase, and/or other characteristics of the sensed light beam. The controller 690 may be configured (e.g., with programming instructions) to provide a user interface (e.g., on a computer screen) for displaying resultant test images and other inspection characteristics as described further herein. The controller 690 may also include one or more input devices (e.g., a keyboard, mouse, joystick) for providing user input, such as changing aperture configuration, viewing detection results data or images, setting up an inspection tool recipe.

In certain embodiments, the controller 690 is configured to carry out inspection techniques. For example, the controller may analyze the detected signals or images in a die-to-die, cell-to-cell, or die-to-database type of inspection. For example, defects may be detected for an imaged area that differs from another reference image area, which is obtained from another die, cell, or simulated from a design database.

Techniques of the present invention may be implemented in any suitable combination of hardware and/or software. The controller 690 typically has one or more processors coupled to input/output ports, and one or more memories via appropriate buses or other communication mechanisms.

The controller 690 may be any suitable combination of software and hardware and is generally configured to control various components of the inspection system 600. For instance, the controller may control selective activation of the illumination source, the illumination or output aperture settings, wavelength band, focus offset setting, polarization settings, etc. The controller 690 may also be configured to receive the image or signal generated by each detector and analyze the resulting image or signal to determine whether defects are present on the sample, characterize defects present on the sample, or otherwise characterize the sample. For example, the controller may include a processor, memory, and other computer peripherals that are programmed to implement instructions of the method embodiments of the present invention.

Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

The sample 634 may also be placed on a stage (not labeled) of the inspection system 600, and the inspection system 600 may also include a positioning mechanism for moving the stage (and sample) relative to the incident beam. By way of examples, one or more motor mechanisms may each be formed from a screw drive and stepper motor, linear drive with feedback position, or band actuator and stepper motor. The one or more positioning mechanisms may also be configured to move other components of the inspection system, such as illumination or collection mirrors, apertures, wavelength filters, polarizers, etc.

It should be noted that the above description and drawings of an inspection system are not to be construed as a limitation on the specific components of the system and that the system may be embodied in many other forms. For example, it is contemplated that the inspection or measurement tool may have any suitable features from any number of known imaging or metrology tools arranged for detecting defects and/or resolving the critical aspects of features of a reticle or wafer. By way of example, an inspection or measurement tool may be adapted for bright field imaging microscopy, darkfield imaging microscopy, full sky imaging microscopy, phase contrast microscopy, polarization contrast microscopy, and coherence probe microscopy. It is also contemplated that single and multiple image methods may be used in order to capture images of the target. These methods include, for example, single grab, double grab, single grab coherence probe microscopy (CPM) and double grab CPM methods. Non-imaging optical methods, such as scatterometry, may also be contemplated as forming part of the inspection or metrology apparatus.

Any suitable lens arrangement may be used to direct the incident beam towards the sample and direct the output beam emanating from the sample towards a detector. The illumination and collection optical elements of the system may be reflective or transmissive. The output beam may be reflected or scattered from the sample or transmitted through the sample. Likewise, any suitable detector type or number of detection elements may be used to receive the output beam and provide an image or a signal based on the characteristics (e.g., intensity) of the received output beam.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. For example, the defect detection characteristic data may be obtained from a transmitted, reflected, or a combination output beam. Accordingly, the present embodiments are to be considered as illustrative and not restrictive, and the invention is not to be limited to the details given herein.

What is claimed is:

1. A method for inspecting a vertical memory stack, comprising:
    on an inspection tool, using incident light having a first wavelength range to detect defects on a surface of the vertical memory stack;
    on the inspection tool, using incident light having a second wavelength range to detect defects on both the surface and throughout a depth of the vertical memory stack; and
    comparing the defects detected using the first and second wavelength range to detect defects only throughout the depth of the vertical memory stack, excluding detects on the surface, as well as to detect defects only on the surface.

2. The method of claim 1, wherein the first wavelength range is selected from one or more of the following ranges: a red-visible range, an ultraviolet range, and a deep ultraviolet range, and wherein the second wavelength is selected from one or more of the following ranges: a blue-visible range, an infrared range, and a near infrared range.

3. The method of claim 2, wherein the first wavelength range is less than about 450 nm and the second wavelength is equal to or greater than about 0.70 microns, and the vertical memory stack comprises a plurality of poly silicon and oxide layers through which incident light at the second wavelength range penetrates and, in response, output light is scattered or reflected back through the poly silicon and oxide layers to be detected by a detector of the inspection tool.

4. The method of claim 3, wherein defects are detected in the vertical memory stack prior to forming word-line (W/L) trenches in the plurality of poly silicon and oxide layers.

5. The method of claim 2, wherein the vertical memory stack comprises a plurality of tungsten and oxide layers having a trench into which incident light at the second wavelength penetrates into the trench.

6. The method of claim 5, wherein the tungsten layers were formed by a process that replaces a plurality of nitride layers.

7. The method of claim 2, wherein the vertical memory stack comprises a plurality of nitride and oxide layers through which incident light at the second wavelength penetrates and, in response, output light is scattered or reflected back through the nitride and oxide layers to be detected by a detector of the inspection tool.

8. The method of claim 7, wherein defects are detected in the vertical memory stack prior to forming word-line (W/L) trenches in the plurality of nitride and oxide layers.

9. The method of claim 2, further comprising vertically or horizontally polarizing the incident light that has the second wavelength range.

10. The method of claim 1, wherein a trench is formed adjacent to the vertical memory stack and the second wavelength range is selected to result in a maximum intensity of light to reach a plurality of depths within the trench.

11. An inspection system for inspecting a vertical semiconductor structure, comprising:
an illumination optics module for generating and directing an incident beam towards a vertical semiconductor structure at both a first wavelength range that is between 700 and 950 nm and a second wavelength range that is less than about 450 nm;
a collection optics module for collecting an output beam at the first wavelength range and at the second wavelength range, the output beam being reflected or scattered from the vertical semiconductor structure in response to the incident beam;
a first detector for detecting the output beam collected at the first wavelength range;
a second detector for detecting the output beam collected at the second wavelength range; and
a controller that is configured to perform the following operations:
detecting defects on a surface of the vertical semiconductor structure based on the detected output beam at the first wavelength range;
detecting defects on both the surface and throughout a depth of the vertical semiconductor structure based on the detected output beam at the second wavelength range; and
comparing the defects detected using the first and second wavelength range to detect defects only throughout the depth of the vertical semiconductor structure, excluding defects on the surface, as well as to detect defects only on the surface.

12. The system of claim 11, wherein the illumination module includes an optical element for splitting an illumination beam into a shorter wavelength beam at the first wavelength range that is directed along a shorter band path and a longer wavelength beam at the second wavelength range that is directed along a longer band path.

13. The system of claim 12, wherein the illumination module further includes a first polarizer in the shorter band path for providing horizontal or vertical polarization in the shorter wavelength beam at the first wavelength range and a second polarizer in the longer band path for providing horizontal or vertical polarization in the longer wavelength beam at the second wavelength range.

14. The system of claim 12, wherein the illumination module further includes a sub-band filter in the longer band paths for applying across each of the first wavelength range so as to bandpass a sub-band in the first wavelength range that has a width that is equal to or less than about 50 nm.

15. The system of claim 12, wherein the optical element for splitting an illumination beam is a dichroic beam splitter for reflecting the incident beam at one of the first and second wavelength ranges and transmitting the incident beam at another one of the first and second wavelength ranges.

16. The system of claim 15, wherein the illumination module further includes a second optical element for recombining the longer and shorter wavelength beams for directing towards the vertical semiconductor structure.

17. The system of claim 16, wherein the illumination module further includes a third optical element for inserting an autofocus beam at a third wavelength range that differs from the first and second wavelength ranges.

18. The system of claim 12, wherein the illumination module includes optical elements in the shorter band path that each minimizes color aberrations across the first wavelength range and optical elements in the longer band path that each minimizes color aberrations across the second wavelength range.

19. The system of claim 11, wherein the vertical semiconductor structure is a vertical memory stack comprising a plurality of poly silicon and oxide layers through which incident light at the second wavelength range penetrates and, in response, output light is scattered or reflected back through the vertical memory stack to be detected by the second detector.

20. The system of claim 11, wherein the vertical semiconductor structure is a vertical memory stack comprising a plurality of tungsten and oxide layers having a trench into which incident light at the second wavelength penetrates into the trench.

* * * * *